US008618127B2

(12) United States Patent
Murphy et al.

(10) Patent No.: US 8,618,127 B2
(45) Date of Patent: *Dec. 31, 2013

(54) METHODS AND COMPOSITIONS FOR ALLEVIATING STUTTERING

(75) Inventors: John J. Murphy, Manhattan, CA (US); Kay Jorgenson D'Orlando, Wayland, MA (US)

(73) Assignee: Endo Pharmaceuticals Solutions Inc., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/489,516

(22) Filed: Jun. 6, 2012

(65) Prior Publication Data

US 2012/0245118 A1 Sep. 27, 2012

Related U.S. Application Data

(63) Continuation of application No. 12/973,515, filed on Dec. 20, 2010, now Pat. No. 8,242,132, which is a continuation of application No. 11/046,706, filed on Feb. 1, 2005, now Pat. No. 7,858,638, which is a continuation of application No. 09/628,803, filed on Jul. 28, 2000, now Pat. No. 6,855,721.

(51) Int. Cl.
*A61K 31/44* (2006.01)

(52) U.S. Cl.
USPC .......................................................... 514/300

(58) Field of Classification Search
USPC .......................................................... 514/300
See application file for complete search history.

(56) References Cited

U.S. PATENT DOCUMENTS

| | | | |
|---|---|---|---|
| 4,401,663 A | 8/1983 | Buckwalter |
| 4,788,055 A | 11/1988 | Fischer |
| 4,816,264 A | 3/1989 | Phillips |
| 4,828,836 A | 5/1989 | Elger |
| 4,834,965 A | 5/1989 | Martani |
| 4,834,985 A | 5/1989 | Elger |
| 4,960,779 A | 10/1990 | Bourzat |
| 4,996,047 A | 2/1991 | Kelleher |
| 5,071,646 A | 12/1991 | Malkowska |
| 5,133,974 A | 7/1992 | Paradissis |
| 5,494,915 A | 2/1996 | Barreau |
| 5,599,936 A | 2/1997 | Barreau |
| 5,676,831 A | 10/1997 | Barreau |

FOREIGN PATENT DOCUMENTS

DK 9800727 A 5/1998

OTHER PUBLICATIONS

U.S. Appl. No. 11/046,706, Non Final Office Action mailed Jul. 14, 2010.
U.S. Appl. No. 11/046,706, Notice of Allowance mailed Aug. 20, 2010.
U.S. Appl. No. 11/046,706, Non Final Office Action mailed Oct. 17, 2008.
U.S. Appl. No. 09/628,803, Office Action mailed Feb. 14, 2001.
U.S. Appl. No. 09/628,803, Final Office Action mailed Apr. 23, 2003.
U.S. Appl. No. 12/973,515, Non Final Office Action mailed Dec. 7, 2011.
U.S. Appl. No. 11/046,706, Non Final Office Action mailed Feb. 19, 2009.
U.S. Appl. No. 09/628,803, Final Office Action mailed Sep. 25, 2001.
U.S. Appl. No. 09/628,803, Non Final Office Action mailed Jul. 30, 2002.
U.S. Appl. No. 11/046,706, Non Final Office Action mailed Mar. 22, 2010.
U.S. Appl. No. 11/046,706, Final Office Action mailed Nov. 12, 2009.
U.S. Appl. No. 09/628,803, Notice of Allowance mailed Oct. 20, 2004.
U.S. Appl. No. 09/628,803, Non Final Office Action mailed Apr. 10, 2001.
U.S. Appl. No. 12/973,515, Notice of Allowance mailed Mar. 9, 2012.
Avis, Kenneth E., "Parenteral Preparations", Remington's Pharmaceutical Sciences, vol. 18, (1990), 27 pgs.
Brady John Paul, "The Pharmacology of Stuttering: A Critical Review", American Journal of Psychiatry, vol. 148, No. 10, (1991), 1309-1316.
Brady, John P., "Dr. Brady Replies [to Costa]", American Journal of Psychiatry, vol. 149, No. 9, (Sep. 1992), 2 pgs.
Brady, John P., "Dr. Brady Replies [to Vink et al.]", American Journal of Psychiatry, vol. 149, No. 5, (1992), 1 pg.
Brady, John Paul, "Drug Induced Stuttering: a Review of the Literature", Journal of Clinical Psychopharmacology, vol. 18, No. 1, (1998).
Brewerton, Timothy D., "Stuttering With Sertraline", The Journal of Clinical Psychiatry, vol. 57, No. 2, (Feb. 20, 1996), 4 pgs.
Christensen, Richard C., "A Case of Sertaline-Induced Stuttering", Journal of Clinical Psychopharmacology, vol. 16, No. 1, (Feb. 1996), 4 pgs.
Costa Daniel, "Antidepressants and the Treatment of Stuttering", The American Journal of Psychiatry, vol. 149, No. 9 (Sep. 1992), 3 pgs.
DiSanto, Anthony R., "Bioavailability and Bioequivalency Testing", Remington's Pharmaceutical Sciences, vol. 18, (1990), 10 pgs.
Doble A., "RP 59037 and RP 60503: Anxiolytic Cyclopyrrolone Derivatives with Low Sedative Potential. Interaction with the y-Aminobutyric Acida/Benzodiazepine Receptor Complex and Behavioral Effects in the Rodent", The Journal of Pharmacology and Experimental Therapeutics, vol. 265, No. 3, (1993), 15 pgs.
Elliott, Richard L., "A Case Report of Alprazolam-Induced Stuttering", Journal of Clinical Psychopharmacology, vol. 5, No. 3, (Jun. 1985), 159-160.

(Continued)

*Primary Examiner* — San-Ming Hui
(74) *Attorney, Agent, or Firm* — RatnerPrestia

(57) ABSTRACT

Methods of treating stuttering include treating people with gamma-aminobutyric acid (GABA) receptor modulators, including cyclopyrrolones. A second active agent may be used with GABA receptor modulators. Active enantiomers, active metabolites, and pharmaceutically acceptable salts of gamma-aminobutyric acid receptor modulators, including cyclopyrrolones, are acceptable components of the compositions. The cyclopyrrolone class of modulators includes pagoclone, suriclone, zopiclone, 2-(7-chloro-2-naphthyridin-1,8-yl)-3-(5-methyl-2-oxohexyl)isoindolin-1-one, 2-(7-chloro-2-naphthyridin-1,8-yl)isoindolin-1-yl-4-acetamidobutyrate, and 2-(7-chloro-1,8-naphthyridin-2yl)-3-(5-methyl-5-hydroxy-2-oxohexyl)-1-isoindolinone.

21 Claims, No Drawings

(56) References Cited

OTHER PUBLICATIONS

Fernandez, Christine, "Clinical Pharmacokinetics of Zopiclone", Clinical Pharmacokinetics, vol. 29, No. 6, (Dec. 1995).
Kiziltan G., "Stuttering May Be a Type of Action Dystonia", Movement Disorders, vol. 11, No. 3 (1996), 8 pgs.
Korpi, Esa R., "GABAa-receptor Subtypes: Clinical Efficacy and Selectivity of Benzodiazepine Site Ligands", the Finnish Medical Society DUODECIM, Annals of Medicine, vol. 29, No. 4 (Aug. 1997), 275-282.
Longer, Mark A., "Sustained-Release Drug Delivery Systems", Remington's Pharmaceutical Sciences, vol. 18, (1990), 20 pgs.
Makela, Eugene H., "Reply [to Christensen et al.]", Journal of Clinical Psychopharmacology, vol. 16, No. 1, (Feb. 1996), 1 pg.
Narin, J.G., "Solutions, Emulsions, Suspensions and Extracts", Remington's Pharmaceutical Sciences, vol. 18, (1990), 28 pgs.
Nurnberg, H. G., "Sildenafil for Sexual Dysfunction in Women Taking Antidepressants", American Journal of Psychiatry, vol. 156, No. 10, (Oct. 1999), 2 pgs.
O'Connor, Robert E., "Powders", Remington's Pharmaceutical Sciences, vol. 18, (1990), 20 pgs.
Porter, Stuart C., "Coating of Pharmaceutical Dosage Forms", Remington's Pharmaceutical Sciences, vol. 18, (1990), 12 pgs.
Rentschler, Gary J., "The Onset of Stuttering Following Drug Overdose", Journal of Fluency Disorders, vol. 9, (1984), 265-284.
Rudnic Edward, "Oral Solid Dosage Forms", Remington's Pharmaceutical Sciences, vol. 18, (1990), 35 pgs.
Sandyk Reuven, "Resolution of Dysarthria in Multiple Sclerosis by Treatment with Weak Electromagnetic Fields", International Journal of Neuroscience, vol. 83, (1995), 81-92.
Schreiber Shaul, "Paroxetine for Secondary Stuttering: Further Interaction of Serotonin and Dopamine", the Journal of Nervous and Mental Disease. vol. 185, No. 7, (1997), 465-467.
Stager, Sheila V., "Fluency Changes in Persons Who Stutter Following a Double Blind Trail of Clomipramine and Desipramine", Journal of Speech and Hearing Research, vol. 38, (Jun. 1995), 516-525.
Swinyard, E. A., "Sedatives and Hypnotics", Remington's Pharmaceutical Sciences, vol. 18, (1990), 1057-1071.
Vadas, Elizabeth B., "Stability of Pharmaceutical Products", Remington's Pharmaceutical Sciences, vol. 18, (1990), 1504-1512.
Vink, H. J.F., "Clonidine and Stuttering", The American Journal of Psychiatry, vol. 149, No. 5, (May 1992), 4 pgs.
Wells, P. G., "Controlled Trial of the Treatment of 36 Stutterers", British Journal of Psychiatry, vol. 119, (1971), 603-604.

METHODS AND COMPOSITIONS FOR ALLEVIATING STUTTERING

CROSS-REFERENCE TO RELATED APPLICATIONS

This application is a continuation of U.S. patent application Ser. No. 12/973,515, filed Dec. 20, 2010, which is a continuation of U.S. patent application Ser. No. 11/046,706, filed Feb. 1, 2005, now U.S. Pat. No. 7,858,638, which is a continuation of U.S. patent application Ser. No. 09/628,803, filed Jul. 28, 2000, now U.S. Pat. No. 6,855,721, the contents of which applications are incorporated by reference herein, in their entireties and for all purposes.

1. FIELD OF THE INVENTION

The present invention relates generally to methods for treating stuttering. The invention also relates to pharmaceutical compositions for treating stuttering, comprising gamma-aminobutyric acid modulators and pharmaceutically acceptable salts thereof, including the cyclopyrrolones, notably pagoclone [(+)2-(7-chloro-1,8-naphthyridine-2-yl)-3-(5-methyl-2-oxo-hexyl)-1-isoindolinone], alone or in combination with one or more pharmaceutically active agents, and a pharmaceutically acceptable carrier.

2. BACKGROUND OF THE INVENTION 2.1. Developmental and Neurogenic Stuttering.

Stuttering is a poorly understood condition marked by frequent repetitions or prolongations of sounds, and an impaired fluency of speech. Accessory features of stuttering, possibly resulting from the attempts of the stutterer to control the stuttering, include blocks in the flow of speech sounds, swallowing, grimacing, tremors of the jaw and tongue, coughing, rapid eye blinking, and jerking movements of the arm or upper trunk. (Brady, J. *Am J Psychiatry*, 1991, 148, 1309). One form, developmental stuttering, often appears in early human childhood or adolescence, and affects predominantly males. An estimated three million Americans are affected and the condition is not dependent on language type or cultural background. A less frequent type is neurogenic stuttering, often a result of head trauma or stroke. Subtle differences between neurogenic and developmental dysfluency may be observed, for example in the repetitive reading test, where sufferers of developmental stuttering often improve by the tenth reading of a passage, but sufferers of neurogenic stuttering do not. A third type is drug-induced stuttering, an increasingly frequent problem.

In the past, stutterers have been treated by a wide variety of methods devised by some of the best minds of the time. Both Hippocrates and Hieronymus Merculialis recommended oral or head surgeries or mutilations. In this century, psychiatric treatments have been tried ranging from operant reinforcement to psychotherapy for presumed unconscious conflicts. However, those who stutter are remarkably well-adjusted, and are similar to those who do not stutter in personality traits. Current methods include speech training and pharmaceutical intervention. The improvement for patients, unfortunately, has been limited.

The spectrum of experimental pharmaceutical interventions has been broad. At times, carbon dioxide inhalation, stimulants (notably methamphetamine), sedatives (in particular, phenobarbital combined with belladonna and ergotamine), an early antihistamine (hydroxyzinc), bromides, thiamine supplements, an antihypertensive (reserpine), the tranquilizer meprobamate, anxiolytics (in particular, benzodiazepines), neuroleptics (including thioridazine, chlorpromazine and trifluoperazine), verapamil, beta-adrenergic blockers (including propranolol, betaxolol, and oxprenolol), an anticonvulsant (carbamazepine), and cholinergic agents (neostigmine and bethanecol) have been tried for stuttering, but all with unsustainable success. Haloperidol has been particularly well studied as an agent for the attenuation of stuttering.

Notably Wells, P. G. et al. *Br J Psychiatry* 1971, 119, 603, reported a placebo-controlled, double-blind study. Wells et al., randomized patients into treatment groups, included objective measures of speech, and found a significant improvement over an eight-week course. Objective criteria in such studies include the length of time to read a standard passage, the number of syllabic repetitions in the process of conveying specific information, the time to explain a solution to a puzzle, and the like. Subsequent studies support a significant improvement in the accessory symptoms of stuttering, including rapid blinking and jerking movements of the upper body, but patient compliance is low because of side-effects including dizziness and dysphoric "medicine-head" symptoms. More significant and disturbing are the long-term detrimental effects haloperidol and other neuroleptics have on voluntary muscle function, known as tardive dyskinesia.

2.2 The $GABA_A$ Neuronal Pathway

One of the main neurotransmitters involved in inhibitory neuronal pathways is gamma-aminobutyric acid or GABA. GABA appears to function mainly at two types of receptors, termed $GABA_A$ and $GABA_B$ receptors, that have different structures. The $GABA_A$ receptor is a GABA-gated chloride ion channel and the $GABA_B$ receptor is a G-protein coupled regulator of potassium conductance. GABA receptors can be modulated by several classes of pharmacologic agents, notably the benzodiazepines, the barbiturates, convulsants, and neurosteroids of the class epiallopregnanolone or epalons. These classes of agents appear to act at different, discrete sites on the $GABA_A$ receptor. Thus, the diversity of effects expressed by these agents ranges from the tranquilizing effects of benzodiazepines, and the sedative effects of barbiturates to the convulsant effects of t-butyl-bicyclophosphorothionate (TBPS), which may act on $GABA_A$ receptors associated with clathrin-coated vesicles. The cyclopyrrolones have demonstrated high affinity for the benzodiazepine binding site on the $GABA_A$ receptor. Some cyclopyrrolones, e.g., pagoclone, have a pharmacological profile consistent with that of a partial agonist at this site. Partial agonists can be efficacious in producing some effects, e.g., anxiolysis, in common with full agonists, but may be less effective in producing others, e.g., sedation. Antagonists, or "blockers," on the other hand, counteract the action of endogenous GABA and exogenous agonists. Inverse agonists decrease the inherent or constitutive stimulation by a receptor in the absence of an agonist. Modulator is a term that includes agonist, partial agonist, inverse agonist, antagonist, neurotransmitter, reuptake inhibitor, and degradation inhibitor. Antagonists are often relatively specific to a particular class of agonists. For example, flumazenil, a benzodiazepine antagonist, blocks the function of benzodiazepines including flunitrazepam, diazepam, pinazepam, prazepam, halazepam, camazepam, and flurazepam.

$GABA_A$ receptor modulators, especially agonists and partial agonists, are also known to act as antiphobics, myorelaxants, anti-epileptics, and by other means. $GABA_A$ receptor modulators act as myorelaxants by decreasing muscle stiffness, decreasing tonus, and reducing voluntary muscle contraction in spasticity. Also some $GABA_A$ modulators have hypnotic, sleep-inducing, amnestic, sedative, and/or anticonvulsant effects. Antagonists of $GABA_A$ receptor function tend to block these effects and may even be anxiogenic or proconvulsant in some individuals.

Many of the $GABA_A$ agonists, in particular the benzodiazepines and the cyclopyrrolones, act to reduce anxiety and induce a sense of calm. In consequence, these agents are termed anxiolytics. It has long been thought that anxiety is a component of stuttering, although the cellular bases for anxiety and stuttering are not at all clear. In contrast, however, the results of placebo-controlled studies of benzodiazepines on stuttering have been inconsistent and disappointing (Brady, supra).

2.3 Drug-Induced Stuttering.

A different approach, that of evaluating drug-induced stuttering, has led to some useful observations, but no cure. Part of the confusion is that many drugs induce stuttering. Several workers have reported that phenothiazines induce stuttering, whether administered alone or with other agents. This drug-induced stuttering was accompanied by akathisia, or a "can't sit still" syndrome. Rentschler, G. J. et al., *J Fluency Disord* 1984, 9, 265 and Elliot, R. I. et al., *J Clin Psychopharmacol* 1985, 5, 159, report stuttering in response to benzodiazepines. Alprazolam, a potent anxiolytic, can induce stuttering (Elliot, supra).

Most of the other cases of drug-induced stuttering are related to inhibition of serotonin uptake, usually with the drugs sertraline or fluoxetine (Brady, J. P. *J Clin Psychopharmacol* 1988, 18, 50), which are also considered to be anxiolytics. The induced stuttering was frequently accompanied by akathisia in these cases as well.

Thus, the state of the art underscores the prevailing and unfilled need for an effective pharmacologic treatment of stuttering. Indeed, the long-standing effort to cure or relieve stuttering has engaged many clinicians over decades, centuries, and even millennia. At least two conclusions may be reached from the wide range of pharmacologic treatments attempted for stuttering. The first is that no clear understanding of the underlying basis for stuttering exists. The study of stuttering is particularly intractable because there exist no animal models and the evaluation of improvement in stuttering is fraught with subjective criteria. The second is that no known agent, or combination of agents, is effective in treating this widespread difficulty.

3. SUMMARY OF THE INVENTION

In a general aspect, the present invention relates to a method for alleviating stuttering, which comprises administering a preparation including an effective amount of one or more GABA receptor modulators.

It is an object of the invention to provide a method for alleviating stuttering, which comprises administering a therapeutically effective dose of a preparation selected from the class of benzodiazepines. Use of active metabolites, active enantiomers, active racemic mixtures, or pharmaceutically acceptable salts of benzodiazepines, as an anti-stuttering medication is contemplated.

It is another object of the invention to provide a method for alleviating stuttering, which comprises administering a therapeutically effective dose of a preparation selected from the class of cyclopyrrolones. The class of cyclopyrrolones includes, but is in no way limited to, pagoclone, suriclone (4-methyl-1-piperazinecarboxylic acid 6-(7-chloro-1,8-naphthyridin-2-yl)-2,3,6,7-tetrahydro-7-oxo-5H-1,4-dithiino[2,3-c]pyrrol-5-yl ester), zopiclone (4-methyl-1-piperazinecarboxylic acid 6-(5-chloro-2-pyridinyl)-6,7-dihydro-7-oxo-5H-pyrrolo-[3.4]pyrazin-5-yl ester), and the compound of U.S. Pat. No. 5,676,831. Use of active metabolites, active enantiomers, active racemic mixtures, or pharmaceutically acceptable salts of cyclopyrrolones, as an anti-stuttering medication is contemplated.

In a yet further object of the invention, pagoclone, its active metabolite, its active enantiomer, an active racemic mixture comprising pagoclone, or pharmaceutically acceptable salts thereof, are contemplated as an anti-stuttering medication.

The present invention is useful for treating, alleviating or preventing stuttering. In an embodiment of the invention, the stuttering can be characterized as being developmental, neurogenic or drug-induced stuttering. Likewise, stuttering is understood to include common stuttering, motor tic, clonic stuttering, dysfluency, speech blockage, impaired phonation, dysarthria, Tourette's syndrome, developmental stuttering, neurogenic stuttering, drug-induced stuttering, logospasm, and the like. There can be different organic, genetic, or developmental origins of the stuttering.

In addition, the present invention also contemplates a pharmaceutical composition suitable for alleviating stuttering in a person afflicted with stuttering which comprises (i) at least one $GABA_A$ receptor modulator, active enantiomer, active metabolite, or pharmaceutically acceptable salt thereof; (ii) at least a second pharmaceutically active agent; and (iii) a pharmaceutically acceptable carrier.

In a more particular aspect, the invention relates to a pharmaceutical composition comprising a $GABA_A$ modulator, including but not limited to pagoclone; suriclone (4-methyl-1-piperazinecarboxylic acid 6-(7-chloro-1,8-naphthyridin-2-yl)-2,3,6,7-tetrahydro-7-oxo-5H-1,4-dithiino[2,3-c]pyrrol-5-yl ester); zopiclone (4-methyl-1-piperazinecarboxylic acid 6-(5-chloro-2-pyridinyl)-6,7-dihydro-7-oxo-5H-pyrrolo-[3.4]pyrazin-5-yl ester); 2-(7-chloro-1,8-naphthyridin-2-yl)-3-(5-methyl-5-hydroxy-2-oxohexyl)-1-isoindolinone, their active enantiomers, their metabolites, or pharmaceutically acceptable salts thereof, alone or in combination with an agent selected from the group consisting of: analgesics, abortifacients, ACE inhibitors, alpha-adrenergic agonists, alpha-adrenergic antagonists, beta-adrenergic agonists, beta-adrenergic antagonists, adrenocortical steroids, adrenocortical suppressants, adrenocorticotropic hormone, alcohol deterrents, aldose reductase inhibitors, aldosterone antagonists, alpha reductase inhibitors, analgesics, androgens, anesthetics, antacids, anthelmintics, antiallergics, antialopecia agents, antiamebics, antiandrogens, antianginals, antiarrhythmics, antiartheriosclerotics, antiarthritics, antiasthmatics, antibiotics, anticholelithogenics, anticholesterimics, anticholinergics, anticoagulants, anticonvulsants, antidepressants, antidiabetics, antidiarrheals, antidiuretics, antidyskinetics, antieczematics, antiemetics, antiepileptics, antiestrogens, antifibrotics, antiflatulents, antifungals, antiglaucoma agents, antihistaminics, antihypertensives, antihypotensives, anti-inflammatories, antimalarials, antimanics, antimigraines, antineoplastics, antiosteoporotics, antiprotozoals, antipruritics, antipsychotics, antivirals, other anxiolytics, bronchodilators, vasodilators, contraceptives, decongestants, diuretics, antimigraines, immunosuppressants, inotropic agents, laxatives, muscle relaxants; supplements, prophylactics of urinary tract infections, and vitamins.

A further object of the invention relates to administration of independent pharmaceutical preparations to the same patient at the same time or different times, preferably at about the same time, and by the same or different modes of administration, where one pharmaceutical preparation comprises a $GABA_A$ receptor modulator and the second pharmaceutical preparation comprises a different agent.

4. DETAILED DESCRIPTION OF THE INVENTION

The present invention contemplates a method of alleviating stuttering in a person, comprising administering an effective stuttering alleviating amount of at least one GABA receptor modulator, an enantiomer of the modulator, an active metabolite of the modulator, or a pharmaceutically acceptable salt of the modulator. One embodiment is a GABA receptor modulator effective at the receptor subtype A.

A method of the present invention includes the treatment of the developmental stuttering and dysfluency that manifests itself, commonly, in adolescence or childhood. Another method of the present invention includes the treatment of stuttering and dysfluency that can occur after trauma to head and body tissues, e.g., those resulting from surgery, injuries, etc. Hence, the pharmaceutical treatment according to the present invention can be administered prior to or after surgery. The present invention contemplates the treatment of drug-induced stuttering as yet another embodiment.

Any mode of administration may be used. It is preferred, however, that the mode of administration is selected from parenteral, oral, vaginal, rectal, nasal, buccal, intravenous, intramuscular, subcutaneous, intrathecal, epidural, intracerebroventricular, transdermal, or combinations thereof. The $GABA_A$ receptor modulator, enantiomer of the modulator, active metabolite of the modulator, or pharmaceutically acceptable salt of the modulator, can act in the central nervous system, including spinal cord, or in the peripheral nervous system, the neuro-muscular system or elsewhere. These agents can have transient action, sustained action or persistent action.

The means of administration will be evident to one skilled in the art, who will know, for example, that some agents must be brain permeant, either in and of themselves, or facilitated by a suitable device or carrier, whereas others should not cross the blood brain barrier.

A wide variety of agents active at $GABA_A$ receptors are suitable for use in the present invention, including cyclopyrrolones, benzodiazepines, general anesthetics, barbiturates, and, neurosteroids, alone or in combination. Suitable components are: allopregnanolone, alphaxalone, alprozolam, amobarbital, aprobarbital, avermectin B, ±baclofen, bicuculline, butabarbital, butalbital, camazepam, cloflubicyne, chlordiazepoxide, clorazepam, chlorazepate, diazepam, diazepam binding inhibitory protein, diazepam binding inhibitory protein fragment, dihydroepiandrosterone, epiallopregnanolone, estazolam, etbicuphat, etbicythionat, etomidate, flucybene, flunitrazepam, flurazepam, halazepam, D-β-hydrastine, isobicyphat, lorazepam, mebicyphat, mephobarbital, methohexital, midazolam, oxazepam, pagoclone, pentobarbitone, pentobarbital, phenobarbital, picrotoxinin, picrotin, pinazepam, prazepam, pregnanolone, pregnenolone, progesterone, propofol, propylbicyphat, quazepam, 2-(7-chloro-2-naphthyridin-1,8-yl)-3-(5-methyl-2-oxohexyl)isoindolin-1-one, also known as RP59037; 2-(7-chloro-2-naphthyridin-1,8-yl)isoindolin-1-yl-4-acetamidobutyrate also known as RP60503, 2-(7-chloro-1,8-naphthyridin-2yl)-3-(5-methyl-5-hydroxy-2-oxohexyl)-1-isoindolinone also known as RPR101769, secobarbital, suriclone, tenazepam, tetrahydrodeoxycorticosterone, tetramethylene sulfotetramide, thiopental, triazolam, zopiclone, and pharmaceutically acceptable salts thereof. Active enantiomers, active metabolites and active racemates of these agents, if they exist, are equally suitable.

The present invention provides a new method of treatment of stuttering using pharmaceutical compounds that preferentially modulate $GABA_A$ receptors In particular, the useful compounds of the invention are cyclopyrrolones according to Formula I, metabolites thereof, enantiomers thereof, racemates thereof, and salts including acid addition salts thereof, alone or in conjunction with one or more other therapeutic agents:

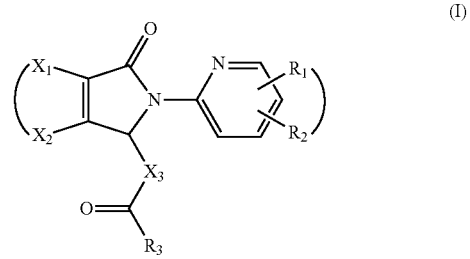

(I)

wherein;

(a) $R_1$ and $R_2$ are the same or different sterically compatible substituents which are selected from the group consisting of: hydrogen; alkyl having 1 to 8 carbon atoms; alkyl having 1 to 8 carbon atoms, and having at least one of nitrogen, oxygen, sulfur, or phosphorus; aryl having 1 to 8 carbon atoms; and aryl having 1 to 8 carbon atoms and having at least one nitrogen, oxygen, sulfur, or phosphorus;

(b) $R_3$ is selected from the group of substituents consisting of: alkyl, alkenyl, alkynyl, alkoxy, alkenoxy, alkynoxy, alkoxyalkyl, alkanoyl, alkenoyl, alkanoyloxy, alkenoyloxy, alkylsulfonyl, alkylsulfinyl, alkylthio, alkanoylamino, alkenoylamino, alkoxycarbonyl, alkenoxycarbonyl, alkoxycarbonylamino, alkoxycarbonylaminoalkyl, aryl, aryl, cycloalkyl having 3 to 6 ring members, cycloalkenyl having 4 to 6 ring members, cycloalkylalkyl having 3 to 6 ring members, cycloalkenylalkyl having 4 to 6 ring members, with the proviso that each the foregoing $R_3$ substituents has up to 8 carbon atoms, trifluoromethyl, nitro, amino, hydroxyl, halogen, aminocarbonyl, cyano, cyanoalkyl having from 2 to 4 carbon atoms, aminocarbonylalkyl having 2 to 4 carbon atoms, aryl, alkaryl, piperazinyl, and methyl-piperazinyl;

(c) $X_1$ and $X_2$ are the same or different sterically compatible substituents which are selected from the group consisting of: hydrogen, alkyl, alkenyl, alkynyl, alkoxy, alkenoxy, alkynoxy, alkoxyalkyl, alkanoyl, alkenoyl, alkanoyloxy, alkenoyloxy, alkylsulfonyl, alkylsulfinyl, alkylthio, alkanoylamino, alkenoylamino, alkoxycarbonyl, alkenoxycarbonyl, alkoxycarbonylamino, alkoxycarbonylaminoalkyl, aryl, cycloalkyl having 3 to 6 ring members, cycloalkenyl having 4 to 6 ring members, cycloalkylalkyl having 3 to 6 ring members, cycloalkenylalkyl having 4 to 6 ring members, with the additional proviso that each of the foregoing $X_1$ and $X_2$ substituents has up to 8 carbon atoms, trifluoromethyl, nitro, amino, hydroxyl, halogen, aminocarbonyl, cyano, cyanoalkyl having from 2 to 4 carbon atoms, aminocarbonylalkyl having 2 to 4 carbon atoms; and (d) $X_3$ is selected from the group consisting of: a methylene; —C(HR$_4$)— where $R_4$ is selected from the group of substituents consisting of alkyl, alkenyl, alkynyl, alkoxy, alkenoxy, alkynoxy, alkoxyalkyl, alkanoyl, alkenoyl, alkanoyloxy, alkenoyloxy, alkylsulfonyl, alkylsulfinyl, alkylthio, alkanoylamino, alkenoylamino, alkoxycarbonyl, alkenoxycarbonyl, alkoxycarbonylamino, alkoxycarbonylaminoalkyl, aryl, cycloalkyl having 3 to 6 ring members, cycloalkenyl having 4 to 6 ring members, cycloalkylalkyl having 3 to 6 ring members, cycloalkenylalkyl having 4 to 6 ring members, with the additional proviso that each of the foregoing $R_4$ substituents has up to 8 carbon atoms, trifluoromethyl, nitro, amino, hydroxyl, halogen, aminocarbonyl, cyano, cyanoalkyl having from 2 to 4 carbon atoms, and aminocarbonylalkyl having 2 to 4 carbon atoms; amino; —N($R_5$)— where $R_5$ is selected from the group of substituents consisting of alkyl, alkenyl, alkynyl, alkoxy, alkenoxy, alkynoxy, alkoxyalkyl, alkanoyl, alkenoyl, alkanoyloxy, alkenoyloxy, alkylsulfonyl, alkylsulfinyl, alkylthio, alkanoylamino, alkenoylamino, alkoxycarbonyl, alkenoxycarbonyl, alkoxycarbonylamino, alkoxycarbonylaminoalkyl, cycloalkyl having 3 to 6 ring members, cycloalkenyl having 4 to 6 ring members, cycloalkylalkyl having 3 to 6 ring members, cycloalkenylalkyl having 4 to 6 ring members, with the additional proviso that each of the foregoing $R_5$ substituents has up to 8 carbon atoms, trifluoromethyl, nitro, amino, hydroxyl, halogen, aminocarbonyl, cyano, cyanoalkyl having from 2 to 4 carbon atoms, and aminocarbonylalkyl having 2 to 4 carbon atoms; sulfur; phosphorus; and oxygen group; pharmaceutically acceptable salts thereof, enantiomers thereof, or metabolites thereof.

The $R_1$ and $R_2$ substituents can be on positions 3, 4, 5, or 6 of the ring.

The invention includes compounds having the structural formula I and the acid addition salts thereof. For medical use, the pharmaceutically acceptable acid addition salts are preferred. The pharmaceutically acceptable acid addition salts are those salts in which the anion does not contribute significantly to the toxicity or pharmacological activity of the salt, and as such, they are the pharmacological equivalents of the bases having the foregoing structural formulas. In some instances, the salts have physical properties which make them more desirable for pharmaceutical formulation purposes such as solubility, lack of hygroscopicity, compressibility with respect to tablet formation and compatibility with other ingredients with which the substances may be used for pharmaceutical purposes. Acid addition salts which do not meet the foregoing criteria for pharmaceutical acceptability, for instance as to toxicity, are sometimes useful as intermediates for isolation and purification of the present substances or for other chemical synthetic purposes such as separation of optical isomers. Such salts are also part of the invention.

The acid addition salts are made by reaction of a base of the structural formula I with the acid, preferably by contact in solution. They also are made by metathesis or treatment with an anion exchange resin whereby the anion of one salt of the substance is replaced by another anion under conditions which allows for separation of the undesired species such as by precipitation from solution or extraction into a solvent or elution from or retention on an anion exchange resin. Pharmaceutically acceptable acids for the purposes of salt formation include hydrochloric, hydrobromic, hydroiodic, citric, acetic, benzoic, phosphoric, nitric, mucic, isethionic, methanesulfonic, p-toluenesulfonic, glucosaccharic, palmitic, heptanoic, oxalic, cyclamic, succinic, malic, fumaric, mandelic, malonic, and others.

The compounds of the present invention shown by the structural formula I contain an asymmetric carbon atom in the cyclopyrrolone ring and occur as optically active isomers as well as racemic mixtures thereof. The present invention is intended to include each of the optically pure, optically active and racemic forms. Some of the substances of the present invention contain an asymmetric carbon atom in the $X_1$, $X_2$, $R_1$, $R_2$, or $R_3$ substituents in formula I, and diastereoisomeric pairs of racemates exist. These forms are also contemplated and included in the methods of the present invention.

Resolution of racemic mixtures to provide the optically active isomers of the foregoing compounds is carried out, for example, by forming a salt with an optically active acid many of which are known to those skilled in the art such as optically active tartaric, mandelic, cholic, O,O-di-p-toluoyl tartaric, and O,O-dibenzoyl tartaric acids, or other acids conventionally employed for this purpose. Separation of optical isomers can be accomplished as disclosed in U.S. Pat. No. 4,960,779 which is incorporated herein by reference.

For the preparation of pharmaceutical compositions containing the compounds of Formula I in the form of dosage units for oral administration, the compound is mixed with a solid, pulverulent carrier such as lactose, sucrose, sorbitol, mannitol, potato starch, corn starch, amylopectin, cellulose derivatives, or gelatin, as well as with glidents such as magnesium stearate, calcium stearate, polyethylene glycol waxes or the like and pressed into tablets. The tablets are used uncoated or coated by known techniques to delay disintegration and absorption in the gastrointestinal tract and thereby provide a sustained action over a longer period. When coated tablets are desired, the above prepared core is coated with a concentrated solution of sugar, which solution may contain e.g., gum arabic, gelatin, talc, titanium dioxide or the like. Furthermore, the tablets are coated with a lacquer dissolved in an easily volatile organic solvent or mixture of solvents and if desired, dye is added to this coating.

In the preparation of soft gelatin capsules consisting of gelatin and e.g., glycerine and the like, the active ingredient is mixed with a vegetable oil and encapsulated in conventional manner. Hard gelatin capsules may contain granules of the active ingredient in combination with a solid, pulverulent carrier such as lactose, saccharose, sorbitol, mannitol, starch (such as e.g. potato starch, corn starch, or amylopectin), cellulose derivatives or gelatin.

Dose units for rectal administration may be prepared in the form of suppositories containing the compound in a mixture with a neutral fat base, or in the form of a gelatin-rectal capsule with a mixture of vegetable oil or paraffin oil.

Liquid preparations suitable for oral administration are suspensions, syrups and elixirs containing from about 0.2% by weight to about 20% by weight of the active ingredient.

A suitable injectable composition is comprised of an aqueous solution of a water soluble pharmaceutically acceptable acid addition salt adjusted to physiologically acceptable pH.

The present invention relates to a pharmaceutical composition for alleviating stuttering, which comprises: (a) an effective amount of a first active ingredient, which comprises at least one $GABA_A$ receptor modulator, including, but not limited to the cyclopyrrolone class of agents, enantiomers, metabolites, and pharmaceutically acceptable salts thereof; optionally, (b) an effective amount of a second active agent; and optionally (c) a pharmaceutically acceptable carrier.

The terms "effective amount;" "therapeutically effective amount," or "pharmaceutically effective amount" of a compound in unit dosage form of the composition depends upon a number of factors. Included among these factors is the quantity of the other ingredients when used. An effective amount of the active ingredient ranges from about 1% to about 100% by weight based on the total weight of the composition but, in any event, is sufficient to observe the anticipated benefit.

By "pharmaceutically acceptable carrier" is meant solid or liquid filler, diluent, or encapsulating substance, which may be safely used in systemic or topical administration. Depending on the particular route of administration, a variety of pharmaceutically acceptable carriers well known in the art may be used, including solid or liquid fillers, diluents, hydrotropies, surface active agents, and encapsulating substances. The amount of a carrier employed in conjunction with the GABA$_A$ receptor modulator is sufficient to 0 provide practical quantity of material per unit dose of GABA$_A$ receptor modulator. Pharmaceutically acceptable carriers for systemic administration, which may be incorporated in the composition of the invention, include sugar, starches, cellulose, vegetable oils, mineral oils, buffers, polyols, alginic acid and the like. Specific pharmaceutically acceptable carriers are described in U.S. Pat. No. 4,401,663; European Patent Application No. 089710; and European Patent Application No, 0068592, which are incorporated herein by reference.

Carriers for parenteral administration may include propylene glycol, pyrrolidone, ethyl oleate, aqueous ethanol and combinations thereof.

Still other representative carriers include acacia, agar, alginates, hydroxyalkylcellulose, hydroxypropyl methylcellulose, carboxymethylcellulose, carboxymethylcellulose sodium, carrageenan, powdered cellulose, guar gum, cholesterol, gelatin, gum agar, gum arabic, gum karaya, gum ghatti, locust bean gum, octoxynol-9, oleyl alcohol, pectin, poly (acrylic acid) and its homologs, polyethylene glycol, polyvinyl alcohol, polyacrylamide, sodium lauryl sulfate, poly(ethylene oxide), polyvinylpyrrolidone, glycol monostearate, propylene glycol monostearate, xanthan gum, tragacanth, sorbitan esters, stearyl alcohol, starch and its modifications. Suitable ranges vary from about 1% to about 50% by weight of the total composition.

Preferred GABA$_A$ receptor modulators are cyclopyrrolones, including, but not limited to, pagoclone; zopiclone; suriclone; 2-(7-chloro-2-naphthyridin-1,8-yl)-3-(5-methyl-2-oxohexyl)isoindolin-1-one, 2-(7-chloro-2-naphthyridin-1,8-yl)isoindolin-1-yl-4-acetamidobutyrate, 2-(7-chloro-1,8-naphthyridin-2-yl)-3-(5-methyl-5-hydroxy-2-oxohexyl)-1-isoindolinone, active metabolites thereof; enantiomers thereof, and pharmaceutically acceptable salts thereof. The most preferred GABA$_A$ receptor modulator is pagoclone, as shown by formula II, where the asterisk indicates the chiral atom, and pharmaceutically acceptable salts thereof.

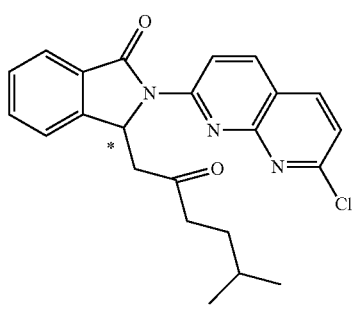

(II)

GABA$_A$ modulators suitable for use in the present invention can exist as salts. In particular, the compounds of the invention can form acid addition salts of pharmaceutically acceptable inorganic or organic acids. Examples of suitable inorganic acids include, but are not limited to, hydrochloric, hydrobromic, sulfuric, phosphoric, or nitric acid. Examples of suitable organic acids include, but are not limited to, aliphatic or aromatic carboxylic or sulfonic acids, for example, acetic, propionic, succinic, glycolic, lactic, fumaric, tartaric, tannic, gluconic, citric, ascorbic, maleic, pyruvic, palmoic, oxalic, dioxalic, nicotinic, methanesulfonic, ethanesulfonic, hydroxyethanesulfonic, benzenesulfonic, p-toluenesulfonic, or naphthalenesulfonic acid. Preferred salts include the hydrochloride, oxalate, fumarate, citrate, tannate, or dioxalate salts.

The GABA$_A$ receptor modulators and salts thereof are discussed in detail in Remington's Pharmaceutical Sciences (in Gennaro, A. et al., Ed., Mack Pub. Co., Easton, Pa. 18th ed. 1990, 1057-1071), the relevant portions of which are incorporated herein by reference.

The pharmaceutical composition of the present invention can have a wide range of GABA$_A$ receptor modulator dosage where a total dosage of about 0.01 to about 1000 mg is administered daily. More preferably, this dosage is about 0.1 mg to about 10 mg. The frequency of doses can vary from about one per day to about two per hour. The dosage can also be adjusted for body weight, from about 0.001 mg/kg body weight/day to about 1.0 mg/kg body weight/day.

The administration of the GABA$_A$ receptor modulator can be by intravenous, intramuscular, subcutaneous, intrathecal, epidural, or intracerebroventricular injection, or parenterally, orally, vaginally, rectally, nasally, buccally, transdermally, and combinations thereof.

The administration of the stuttering alleviating or ameliorating substance to the patient can be conducted in conjunction with treatment for other ailments with the second active agent, or other agents. Effective dosage levels can vary widely; actual amounts will depend on the agents used and the state and diagnosis of the patient being treated. As those skilled in the art would recognize, many factors that modify the action of the stuttering alleviating composition and second active agents herein will be taken into account by the treating physician including, but not limited to, such factors as age, body weight, sex, diet, and condition of the patient, time of administration, rate and route of administration, psychiatric condition, other diseases, and so forth. Titration of dosage for individual patients, up to the maximal dose permits attainment of functionally effective doses. Optimal dosages for a given set of conditions can be ascertained by those skilled in the art using conventional dosage determination tests in view of experimental data provided herein.

The stuttering alleviating substance of the instant invention will ordinarily be formulated with one or more pharmaceutically acceptable ingredients in accordance with known and acceptable practice. The stuttering alleviating substance can be formulated as a liquid, powder, aerosol, elixir, injectable solution, etc. Formulations for oral use can be provided as hard gelatin capsules wherein the stuttering alleviating substance is mixed with an inert solid diluent such as calcium carbonate, phosphate, or kaolin or, preferably, as soft gelatin capsules wherein the stuttering alleviating substance is mixed with an oleaginous medium, e.g., liquid paraffin or soybean oil.

Aqueous suspensions can contain the stuttering alleviating substance in an admixture with pharmaceutically acceptable excipients such as: suspending agents, like carboxymethylcellulose, methylcellulose, hydroxypropylmethylcellulose, sodium alginate, polyvinylpyrrolidone, gum tragacanth, gum acacia; dispersing or wetting agents such as naturally occurring phosphatide, e.g., lecithin; or condensation products of an alkaline oxide with fatty acids, e.g., polyoxyethylene stearate or condensation products of ethylene oxide with partial esters derived from fatty acids and hexitol, e.g., polyoxyethylene sorbitol monooleate; or condensation products of ethylene oxide with partial esters derived from fatty acids and hexitol anhydrides, e.g., polyoxyethylene sorbitan monooleate. Such aqueous suspensions can also contain one or more preservatives, e.g., ethyl or n-propyl-p-hydroxybenzoate; or one or more coloring agents, flavoring agents and sweetening agents such as saccharose, saccharin or sodium or calcium cyclamate.

In the preparation of aqueous suspensions, water is added to dispersible powders and granules to provide the stuttering alleviating substance in an admixture with dispersing or wetting agent, suspending agent and one or more preservatives. Suitable dispersing or wetting agents and suspending agents are exemplified by those already mentioned above. Additional excipients include sweetening, flavoring and coloring agents. Syrups and elixirs can be formulated with sweetening agents such as glycerol, sorbitol or sucrose. Such formulations can contain demulcent, preservative, flavoring and coloring agents.

The stuttering alleviating agent can be administered in a sustained release formulation. Methods for sustained release dosage forms are advantageously provided in U.S. Pat. Nos. 4,788,055; 4,816,264; 4,828,836; 4,834,965; 4,834,985; 4,996,047; 5,071,646; and 5,133,974, which are incorporated herein by reference.

The compositions of the invention have pharmacological advantages that render them useful for alleviating stuttering. In this application, at least one GABA receptor modulator and one or more second active agent may be administered according to any convenient or effective method for introducing foreign substances into the blood stream of mammals, such as by oral, rectal, nasal, buccal, vaginal or parenteral routes. The effective dose levels may be administered on a regimen of about 1 to about 6 times a day. The pharmaceutical formulation of the invention can be in dosage forms such as pills, capsules, powders or granules for oral administration. The compounds can be conveniently administered in unit dosage form and can be prepared by any of the methods well known in the pharmaceutical art, for example as described in Remington's Pharmaceutical Sciences, supra, 1451-1459, 1504-1512, 1519-1570, and 1615-1693, which are incorporated herein by reference.

The compounds of the invention can be formulated into pharmaceutical compositions of an admixture with pharmaceutically acceptable carriers. As discussed above, the compositions may be prepared for use by or in parenteral, that is, subcutaneous, intramuscular, or intravenous, administration, particularly in the form of liquid suspensions. Also, the composition can be prepared for oral administration, particularly in the form of tablets or capsules, or intranasally, particularly in the form of powders, nasal drops or aerosols. The composition can also be prepared for use in vaginal or rectal administration. Formulations for parenteral administration may contain as common excipients, sterile water, or saline, polyalkylene glycols such as polyethylene glycol, oils of vegetable origin, hydrogenated naphthalenes and the like. Formulations for vaginal or rectal administration, e.g., suppositories may contain as excipients, for example, polyalkylene glycols such as polyethylene glycol, petroleum jelly, cocoa butter and the like. Formulations for inhalation administration may be solid and contain excipients, for example, lactose, or may be aqueous or oily solutions for administration in the form of nasal drops. For buccal administration, typical excipients include sugars, calcium stearate, magnesium stearate, pregelatinated starch and the like.

For oral administration, a pharmaceutically acceptable composition can be formed by incorporation of any of the normally employed excipients, oral dose extenders or carriers such as for example, pharmaceutical grades of mannitol, lactose, starch, magnesium stearate, sodium saccharin, talcum, cellulose, glucose, sucrose, magnesium, carbonate and the like. Such compositions can take the form of solution, suspension, tablets, pills, capsules, powders, sustained release formulations and the like.

To produce tablets or dragée cores, the active substances are combined with, e.g., solid pulverulent carriers such as lactose, saccharose, sorbitol, mannitol; starches such as potato starch, maize starch, amylopectin, also laminaria powder or citrus pulp powder; cellulose derivatives or gelatin, optionally with the addition of lubricants such as magnesium or calcium stearate or polyethylene glycol of suitable molecular weight to form tablets or dragée cores. The latter are coated, e.g., with concentrated sugar solutions which can also contain, e.g., gum arabic, talcum, titanium dioxide, or with lacquer dissolved in a mixture of solvents. Other suitable oral dosage units are hard gelatin capsules as well as soft, closed capsules from a gelatin softener such as glycerol.

Examples of dosage units for rectal administration are suppositories that comprise a combination of at least one $GABA_A$ receptor modulator, one or more second active agents and a carrier suppository foundation. Also suitable are a gelatin rectal capsules, which contain a combination of at least one of the above substances with polyethylene glycol of suitable molecular weight as carrier.

Ampoules for parenteral, particularly intramuscular and also intravenous administration, preferably contain at least one $GABA_A$ receptor modulator and one or more second active agents. If necessary, suitable stabilizing agents and/or buffer substances are added to the ampule solutions.

These compounds can be encapsulated, tableted or prepared in a emulsion or syrup for oral administration. Pharmaceutically acceptable solid or liquid carriers can be added to enhance or stabilize the composition, or to facilitate preparation of the composition. Liquid carriers include syrup, peanut oil, olive oil, sesame oil, vegetable oil, mineral oil, soybean oil, cottonseed oil, glycerin, saline, ethanol, and water. Solid carriers include starch, lactose, calcium sulfate dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation is in the form of a syrup, elixir, emulsion or an aqueous or non-aqueous suspension. Such a liquid formulation can be administered directly by mouth or filled into a soft gelatin capsule.

5. EXAMPLES

The following specific examples are provided to better assist the reader in the various aspects of practicing the present invention. As these specific examples are merely illustrative, nothing in the following descriptions should be construed as limiting the invention in any way. Such limitations are, of course, defined solely by the accompanying claims.

6.1 Improvement of the Stuttering of a Patient Treated with Pagoclone.

A 26-year old female patient is enrolled in a clinical trial examining the efficacy and safety of pagoclone, a drug which works at the $GABA_A$ receptor, in the treatment of panic disorder, an anxiety disorder. She experiences a significant reduction in her fairly severe stuttering problem while she is taking the pagoclone. The double-blind placebo-controlled trial conceals the drug type until the conclusion of the trial. During the trial the patient is taking 0.60 mg pagoclone/day (0.20 mg t.i.d.). The patient had never before experienced this sort of an effect on her stuttering and she had taken, in the past, other anti-anxiety medications for her psychiatric condition, none of which had such an effect on her stuttering. During the trial, both she and the clinician treating her in the clinical trial notice the reduction in her stuttering, which is documented at her week 2 visit. Her stuttering returns to the pre-drug level within a day of stopping the pagoclone. She also experiences a reduction in her anxiety and improvement in her psychiatric condition. During the trial she also is taking ibuprofen and a prophylactic for urinary tract infections.

6.2 Large-Scale Trial Treatment, with Pagoclone, of Patients Suffering from Developmental Stuttering.

Patients with stuttering problems are enrolled in a clinical trial examining the efficacy and safety of pagoclone in the treatment of developmental stuttering. The open-label trial is administered by physicians. During the trial one group of twenty patients is taking 0.60 mg pagoclone/day (0.20 mg t.i.d.), another group is taking 0.20 mg pagoclone/day, and another group is taking a placebo. The patients have never before experienced relief of stuttering by a medication. During the trial, both the patients and the clinicians treating them in the clinical trial monitor the stuttering by a battery of objective tests, and document each case.

6.3 Large-Scale Treatment, with Selected $Gaba_4$ Modulators, of Patients Suffering from Stuttering.

Patients with stuttering problems are enrolled in a clinical trial examining the efficacy and safety of zopiclone, suriclone, diazepam, propofol, alphaxalone, and pentobarbital, drugs which work at the $GABA_A$ receptor, in the treatment of developmental stuttering. The patients are randomly assigned to one of eight groups. The double-blind placebo-controlled trial conceals the drug type until the conclusion of the trial. During the trial each group of patients is taking a therapeutically effective dose of one agent or is taking the placebo. The patients have never before experienced relief of stuttering by a medication. During the trial, both the patients and the clinicians treating them in the clinical trial monitor the stuttering by objective evaluations of dysfluency, and document each case.

6.4 Large-Scale Trial Treatment, with Pagoclone and a Second Active Agent, of Patients Suffering from Stuttering.

Patients with stuttering problems are enrolled in a clinical trial examining the efficacy and safety of pagoclone and a second active agent in the treatment of developmental stuttering. The second agents are ibuprofen, UTI Plus, propanolol, minoxidil, estrogen, citicoline, ergotamine, and pregnanolone. Patients are randomly assigned to one of nine groups. The double-blind placebo-controlled trial conceals the drug type until the conclusion of the trial. During the trial all patients are taking 0.01 mg pagoclone/kg body weight/day. Each group is provided a pharmaceutically effective daily dose of one of the eight second active agents, and one group is provided a placebo. The patients have never before experienced relief of stuttering from a medication. During the trial, both the patients and the clinicians treating them in the clinical trial monitor the stuttering by a battery of objective criteria, and document each case.

What is claimed is:

1. A method for alleviating stuttering, in a subject in need thereof, comprising: administering a therapeutically effective dose of a gamma-aminobutyric acid receptor modulator, its pharmaceutically acceptable salts, enantiomers, or metabolites thereof, wherein the modulator is selected from the group consisting of alprozolam, camazepam, clorazepam, chlorazepate, diazepam, estazolam, flunitrazepam, flurazepam, halazepam, lorazepam, midazolam, oxazepam, pagoclone, pinazepam, prazepam, quazepam, 2-(7-chloro-2-naphthyridin-1,8-yl)-3-(5-methyl-2-oxohexyl)isoindolin-1-one, 2-(7-chloro-2-naphthyridin-1,8-yl)isoindolin-1-yl-4-acetamidobutyrate, 2-(7-chloro-1,8-naphthyridin-2-yl)-3-(5-methyl-5-hydroxy-2-oxohexyl)-1-isoindolinone, suriclone, tenazepam, triazolam, zopiclone, pharmaceutically acceptable salts thereof, enantiomers thereof, or metabolites thereof, and any mixtures thereof.

2. A method for alleviating stuttering, in a subject in need thereof, comprising: administering a therapeutically effective dose of a gamma-aminobutyric acid receptor modulator, its pharmaceutically acceptable salts, enantiomers, or metabolites thereof, wherein the modulator is a cyclopyrrolone having the formula (I):

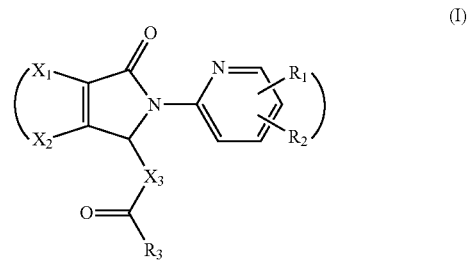

wherein:
$R^1$ and $R^2$ are sterically compatible substituents which are independently selected from the group consisting of: hydrogen, alkyl having 1 to 8 carbon atoms, alkyl having 1 to 8 carbon atoms comprising at least one of nitrogen, oxygen, sulfur, or phosphorus, aryl having 1 to 8 carbon atoms, and aryl having 1 to 8 carbon atoms and comprising at least one nitrogen, oxygen, sulfur, or phosphorus;

$R^3$ is selected from the group consisting of alkyl, alkenyl, alkynyl, alkoxy, alkenoxy, alkynoxy, alkoxyalkyl, alkanoyl, alkenoyl, alkanoyloxy, alkenoyloxy, alkylsulfonyl, alkylsulfinyl, alkylthio, alkanoylamino, alkenoylamino, alkoxycarbonyl, alkenoxycarbonyl, alkoxycarbonylamino, alkoxycarbonylaminoalkyl, cycloalkyl having 3 to 6 ring members, cycloalkenyl having 4 to 6 ring members, cycloalkylalkyl having 3 to 6 ring members, cycloalkenylalkyl having 4 to 6 ring members, with the proviso that each of the foregoing substituents has up to 8 carbon atoms, trifluoromethyl, nitro, amino, hydroxyl, halogen, aminocarbonyl, cyano, cyanoalkyl having from 2 to 4 carbon atoms, aminocarbonylalkyl having 2 to 4 carbon atoms, aryl, alkaryl, piperazinyl, and methylpiperazinyl;

$X^1$ and $X^2$ are sterically compatible substituents which are independently selected from the group consisting of hydrogen, alkyl, alkenyl, alkynyl, alkoxy, alkenoxy, alkynoxy, alkoxyalkyl, alkanoyl, alkenoyl, alkanoyloxy, alkenoyloxy, alkylsulfonyl, alkylsulfinyl, alkylthio, alkanoylamino, alkenoylamino, alkoxycarbonyl, alkenoxycarbonyl, alkoxycarbonylamino, alkoxycarbonylaminoalkyl, cycloalkyl having 3 to 6 ring members, cycloalkenyl having 4 to 6 ring members, cycloalkylalkyl having 3 to 6 ring members, cycloalkenylalkyl having 4 to 6 ring members, with the additional proviso that each of the foregoing substituents has up to 8 carbon atoms, trifluoromethyl, nitro, amino, hydroxyl, halogen, aminocarbonyl, cyano, cyanoalkyl having from 2 to 4 carbon atoms, aminocarbonylalkyl having 2 to 4 carbon atoms; and $X^3$ is selected from the group consisting of a
  methylene;
    —C(HR⁴)— where
      R⁴ is selected from the group consisting of alkyl, alkenyl, alkynyl, alkoxy, alkenoxy, alkynoxy, alkoxyalkyl, alkanoyl, alkenoyl, alkanoyloxy, alkenoyloxy, alkylsulfonyl, alkylsulfinyl, alkylthio, alkanoylamino, alkenoylamino, alkoxycarbonyl, alkenoxycarbonyl, alkoxycarbonylamino, alkoxycarbonylaminoalkyl, cycloalkyl having 3 to 6 ring members, cycloalkenyl having 4 to 6 ring members, cycloalkylalkyl having 3 to 6 ring members, cycloalkenylalkyl having 4 to 6 ring members, with the additional proviso that each of the foregoing substituents has up to 8 carbon atoms, trifluoromethyl, nitro, amino, hydroxyl, halogen, aminocarbonyl, cyano, cyanoalkyl having from 2 to 4 carbon atoms, aminocarbonylalkyl having 2 to 4 carbon atoms;
  amino;
    —N(R⁵)— where
      R⁵ is selected from the group consisting of alkyl, alkenyl, alkynyl, alkoxy, alkenoxy, alkynoxy, alkoxyalkyl, alkanoyl, alkenoyl, alkanoyloxy, alkenoyloxy, alkylsulfonyl, alkylsulfinyl, alkylthio, alkanoylamino, alkenoylamino, alkoxycarbonyl, alkenoxycarbonyl, alkoxycarbonylamino, alkoxycarbonylaminoalkyl, cycloalkyl having 3 to 6 ring members, cycloalkenyl having 4 to 6 ring members, cycloalkylalkyl having 3 to 6 ring members, cycloalkenylalkyl having 4 to 6 ring members, with the additional proviso that each of the foregoing substituents has up to 8 carbon atoms, trifluoromethyl, nitro, amino, hydroxyl, halogen, aminocarbonyl, cyano, cyanoalkyl having from 2 to 4 carbon atoms, aminocarbonylalkyl having 2 to 4 carbon atoms;
  sulphur;
  phosphorus;
  and oxygen group;
  pharmaceutically acceptable salts thereof, enantiomers thereof, or metabolites thereof.

3. The method according to claim 2, wherein $R^1$ and $R^2$ are covalently bonded to form a polycyclic structure.

4. The method according to claim 2, wherein the cycloalkyl of $R^3$, $R^4$, $R^5$, $X^1$, and $X^2$ independently have 1 to 3 alkyl substituents.

5. The method according to claim 2, wherein the cycloalkenyl of $R^3$, $R^4$, $R^5$, $X^1$, and $X^2$ are the same or different, and each have up to 3 alkyl substituents.

6. The method according to claim 2, wherein cycloalkylalkyl of $R^3$, $R^4$, $R^5$, $X^1$, and $X^2$ are the same or different, and each have up to 3 alkyl substituents.

7. The method according to claim 2, wherein cycloalkenylalkyl of $R^3$, $R^4$, $R^5$, $X^1$, and $X^2$ are the same or different, and each have up to 3 alkyl substituents.

8. The method according to claim 2, wherein $X^1$ and $X^2$ are covalently bonded to form a polycyclic structure.

9. The method according to claim 1, additionally comprising a pharmaceutically acceptable carrier.

10. The method according to claim 1, wherein said modulator is effective at the receptor subtype A.

11. The method according to claim 1, wherein said modulator is an agonist of the receptor subtype A.

12. The method according to claim 1, wherein said administration is performed parenterally, orally, vaginally, rectally, nasally, buccally, intravenously, intramuscularly, subcutaneously, intrathecally, epidurally, transdermally, intracerebroventricularly, or combinations thereof.

13. The method according to claim 1, wherein the dose is about 0.01 to about 1000 mg.

14. The method according to claim 13, wherein the dose is about 0.1 to about 10 mg.

15. The method according to claim 1, wherein said modulator comprises pagoclone, suriclone, zopiclone, 2-(7 chloro-2-naphthyridin-1,8-yl)-3-(5-methyl-2-oxohexyl)isoindolin-1-one, 2-(7-chloro-2-naphthyridin-1,8-yl)isoindolin-1-yl-4-acetamidobutyrate, 2-(7-chloro-1,8-naphthyridin-2-yl)-3-(5-methyl-5-hydroxy-2-oxohexyl)-1-isoindolinone, pharmaceutically acceptable salts thereof, enantiomers thereof, or metabolites thereof.

16. The method according to claim 15, wherein the modular comprises pagoclone.

17. The method according to claim 16, wherein the pagoclone is administered at least once daily.

18. The method according to claim 1, wherein the subject is suffering from stuttering, motor tic, clonic stuttering, dysfluency, speech blockage, dysarthria, Tourette's syndrome, or logospasm.

19. A method of alleviating stuttering, in a subject in need thereof, comprising: administering a therapeutically effective dose of gamma-amino butyric acid receptor modulator, wherein the modulator is selected from the group consisting of alprozolam, camazepam, clorazepam, chlorazepate, diazepam, estazolam, flunitrazepam, flurazepam, halazepam, lorazepam, midazolam, oxazepam, pagoclone, pinazepam, prazepam, quazepam, 2-(7-chloro-2-naphthyridin-1,8-yl)-3-(5-methyl-2-oxohexyl)isoindolin-1-one, 2-(7-chloro-2-naphthyridin-1,8-yl)isoindolin-1-yl-4-acetamidobutyrate, 2-(7-chloro-1,8-naphthyridin-2-yl)-3-(5-methyl-5-hydroxy-2-oxohexyl)-1-isoindolinone, suriclone, tenazepam, triazolam, zopiclone, pharmaceutically acceptable salts thereof, enantiomers thereof, or metabolites thereof, and any mixtures thereof, and a second active ingredient.

20. A method for alleviating stuttering, in a subject in need thereof, comprising: administering a dose of pagoclone in a pharmaceutically acceptable carrier, where the pagoclone is present in an amount between about 0.1 mg and about 10 mg.

21. The method according to claim 1, wherein the modulator is 2-(7-chloro-1,8-naphthyridin-2-yl)-3-(5-methyl-5-hydroxy-2-oxohexyl)-1-isoindolinone.

* * * * *